(12) United States Patent
Park et al.

(10) Patent No.: US 10,617,398 B2
(45) Date of Patent: Apr. 14, 2020

(54) ADJUSTABLE-BENDING STIFFNESS STEERABLE NEEDLE, BUCKLING-PREVENTING STEERABLE NEEDLE, AND STEERABLE NEEDLE SYSTEM INCLUDING SAME

(71) Applicant: INDUSTRY FOUNDATION OF CHONNAM NATIONAL UNIVERSITY, Gwangju (KR)

(72) Inventors: Sukho Park, Gwangju (KR); Jongoh Park, Goyang-si (KR); Byungjeon Kang, Gwangju (KR)

(73) Assignee: Industry Foundation of Chonnam National University, Gwangju (KR)

(*) Notice: Subject to any disclaimer, the term of this patent is extended or adjusted under 35 U.S.C. 154(b) by 219 days.

(21) Appl. No.: 15/488,326

(22) Filed: Apr. 14, 2017

(65) Prior Publication Data
US 2018/0000466 A1    Jan. 4, 2018

(30) Foreign Application Priority Data

Jul. 4, 2016  (KR) .................. 10-2016-0084329
Jul. 4, 2016  (KR) .................. 10-2016-0084333

(51) Int. Cl.
*A61B 17/32*  (2006.01)
*A61B 10/02*  (2006.01)
*A61B 34/00*  (2016.01)

(52) U.S. Cl.
CPC .......... *A61B 10/0233* (2013.01); *A61B 34/73* (2016.02); *A61B 2010/0208* (2013.01)

(58) Field of Classification Search
CPC .......... A61F 9/00763; A61B 17/32002; A61B 17/320758; A61B 10/02; A61B 10/0233; A61B 2010/0208; A61B 2010/045
See application file for complete search history.

(56) References Cited

U.S. PATENT DOCUMENTS

| | | | |
|---|---|---|---|
| 2006/0074383 A1 | 4/2006 | Boulais | |
| 2007/0016067 A1 | 1/2007 | Webster, III et al. | |
| 2016/0100860 A1* | 4/2016 | Lenker | A61B 17/3478 604/95.01 |

FOREIGN PATENT DOCUMENTS

| | | |
|---|---|---|
| KR | 10-2014-0026959 A | 3/2014 |
| KR | 10-1506932 B1 | 4/2015 |

* cited by examiner

*Primary Examiner* — Melanie R Tyson
(74) *Attorney, Agent, or Firm* — Rabin & Berdo, P.C.

(57) ABSTRACT

Disclosed herein are an adjustable-bending stiffness steerable needle, a buckling-preventing steerable needle, and a steerable needle system including the same. The adjustable-bending stiffness steerable needle includes a cylindrical core wire, a tip portion, a needle shaft, a compression spring, and a rigid shaft. The tip portion has a bevel shape, and is connected to the front end of the core wire. The needle shaft is disposed such that one end thereof is separable from the tip portion and the needle shaft surrounds the core wire. The compression spring is fastened to the other end of the needle shaft, and is configured such that the core wire passes therethrough. The rigid shaft is connected to the core wire having passed through the compression spring, and is also connected to the compression spring. The needle shaft includes a plurality of hollow tube elements that is separable from each other.

8 Claims, 11 Drawing Sheets

ADJUSTABLE-BENDING STIFFNESS STEERABLE NEEDLE, BUCKLING-PREVENTING STEERABLE NEEDLE, AND STEERABLE NEEDLE SYSTEM INCLUDING SAME

BACKGROUND

1. Technical Field

The present invention relates generally to a steerable needle, and more particularly to an adjustable-bending stiffness steerable needle that can be easily and accurately steered to a target region to be treated through the passive or active control of bending stiffness during an intervention treatment procedure within a soft tissue.

Furthermore, the present invention relates generally to a steerable needle, and more particularly to a buckling-preventing steerable needle that can minimize damage to a soft tissue through the prevention of a buckling phenomenon, which may occur in a flexible needle, during an intervention treatment procedure within the soft tissue.

2. Description of the Related Art

In general, steerable needles are medical devices that are used to perform intervention treatment procedures, such as the tissue biopsies of the lesions of the breast, the abdomen, and various organs, the treatment of a lesion using high frequency, proximate treatment, medicine delivery, etc., within soft tissues by using elongated flexible needles. In particular, steerable needles have advantages in that they can expand a small acceptable area attributable to the limited mechanical characteristics of conventional stiff needles and also can improve the efficiency and accuracy of the approach of needles to targets.

As a related conventional art, U.S. Patent Application Publication No. US 2007/0016067 A1 discloses a technology for controlling a needle by using bending force provide to a bevel-shaped end while the needle having the bevel-shaped end is moving through a tissue, as shown in FIG. 1.

Various types of research are being conducted into a rectilinear steerable needle using external moment to reach a desired location, a steerable needle using the control of the relative locations of a plurality of sliding segments, etc. in addition to the above-described steerable needle using the bending phenomenon of a flexible needle including a tip having an obliquely cut end.

However, it is impossible to control the intrinsic bending stiffness of the conventional steerable needles, and thus the curvature of a path along which steering can be performed is small and it is difficult to perform accurate steering control due to the non-uniform characteristics of soft tissues.

Steerable needles use elongated flexible needles having low bending stiffness. In FIG. 1, a flexible needle 110 having an oblique end is shown. Referring to the upper view of FIG. 1, the flexible needle 110 is composed of a very thin, flexible wire or tube, and one end of the flexible needle 110 is composed of an oblique bevel tip. As shown in the lower view of FIG. 1, when the flexible needle 110 passes through a needle guide 118 and is then inserted into a soft tissue 112, the flexible needle 110 is steered and inserted along a planned path 114 by using the bending phenomenon of the needle that is generated by the interactive force between the oblique end and the soft tissue 112.

However, due to a small steering angle, it is difficult to insert the flexible needle 100 along a path having a large curvature. Furthermore, when the distance to which the needle is inserted is long or the needle encounters a hard region within a non-uniform soft tissue, an abrupt buckling phenomenon occurs within the tissue.

In other words, the tip of the needle is not moved any farther, and the insertion force used to insert the needle becomes a cause of the occurrence of the buckling phenomenon of the needle within the soft tissue. As shown in the lower view of FIG. 1, a buckling phenomenon in which the flexible needle 110 deviates from the planned path 114 occurs.

When the buckling phenomenon of the needle occurs, serious damage to the soft tissue, such as the cutting or tearing of the soft tissue, may be caused. When a flexible needle having higher bending stiffness is used due to concern about such a buckling phenomenon, the curvature of a path along which steering can be performed becomes low, and thus a limitation arises in that applicable treatment procedures are limited due to a small acceptable area.

Therefore, there are needs for a steerable needle capable of controlling bending stiffness and accurately controlling steering and a steerable needle capable of preventing a buckling phenomenon, which can overcome the above-described problems.

SUMMARY

The present invention has been contrived to overcome the above-described problems, and an object of the present invention is to provide an adjustable-bending stiffness steerable needle that is capable of more accurately and more effectively providing an intervention treatment procedure within a soft tissue through the active or passive control of the bending stiffness of the needle within the soft tissue.

Another object of the present invention is to provide a steerable needle that can provide the improved steering performance of the needle within a soft tissue and also can prevent the buckling phenomenon of the needle in order to enable an intervention treatment procedure to be safely performed within a soft tissue.

Objects of the present invention are not limited to the above-described objects, and other objects that have not been described above will be clearly appreciated by those skilled in the art from the follow description.

In accordance with an aspect of the present invention, there is provided an adjustable-bending stiffness steerable needle, including: a cylindrical core wire; a tip portion configured to have a bevel shape, and connected to the front end of the core wire; a needle shaft disposed such that one end thereof is separable from the tip portion and the needle shaft surrounds the core wire; a compression spring fastened to the other end of the needle shaft, and configured such that the core wire passes therethrough; and a rigid shaft connected to the core wire having passed through the compression spring, and also connected to the compression spring; wherein the needle shaft includes a plurality of hollow tube elements that are separable from each other.

In accordance with another aspect of the present invention, there is provided an adjustable-bending stiffness steerable needle, including: a cylindrical core wire; a tip portion configured to have a bevel shape, and connected to a front end of the core wire; a needle shaft disposed such that one end thereof is separable from the tip portion and the needle shaft surrounds the core wire; a compression spring fastened to the other end of the needle shaft, and configured such that the core wire passes therethrough; and a rigid shaft connected to the core wire having passed through the compression spring, and also connected to the compression spring; wherein the needle shaft includes a plurality of hollow tube elements that are separable from each other, and the tip portion has a cone-shaped permanent magnet, steerable by an external magnetic field generation mechanism, instead of the bevel shape.

At least one of both ends of the compression spring may be configured to be slidable along the outer circumferential surface of the core wire so that the compression spring can be compressed between the needle shaft and the right shaft.

In accordance with another aspect of the present invention, there is provided an adjustable-bending stiffness steerable needle system, including: the above-described steerable needle; and an insertion driving unit configured to insert the steerable needle into a tissue.

The adjustable-bending stiffness steerable needle system may further include a rotation driving unit configured to rotate the steerable needle within a tissue, and a compressing mechanism configured to allow the compression spring to be selectively extended and compressed with respect to the rigid shaft.

In accordance with another aspect of the present invention, there is provided a steerable needle, including: a tip portion; a cylindrical core wire configured such that one end thereof is connected to the tip portion; a rigid shaft connected to the other end of the core wire; and a plurality of tube elements disposed between the tip portion and the rigid shaft in a line in an axial direction while surrounding the core wire; wherein one end portion of the tip portion has a bevel shape, and the plurality of tube elements is configured to be movable via gaps formed between the plurality of tube elements.

The steerable needle may further include a driving unit including at least one of an insertion mechanism configured to insert the steerable needle into a tissue and a rotation mechanism configured to rotate the steerable needle around an axial direction.

The rotation mechanism may be operable such that only the tip portion and the core wire are rotated in the state in which the plurality of tube elements is stationary.

The one end portion of the tip portion may have a cone shape, and may include a permanent magnet steerable by an external magnetic field generation mechanism.

The steerable needle may further include an insertion mechanism configured to insert the steerable needle into a tissue.

BRIEF DESCRIPTION OF THE DRAWINGS

The above and other objects, features and advantages of the present invention will be more clearly understood from the following detailed description taken in conjunction with the accompanying drawings, in which:

FIG. 5b is an enlarged view of portion C of FIG. 5a;

DETAILED DESCRIPTION

Figure 1:
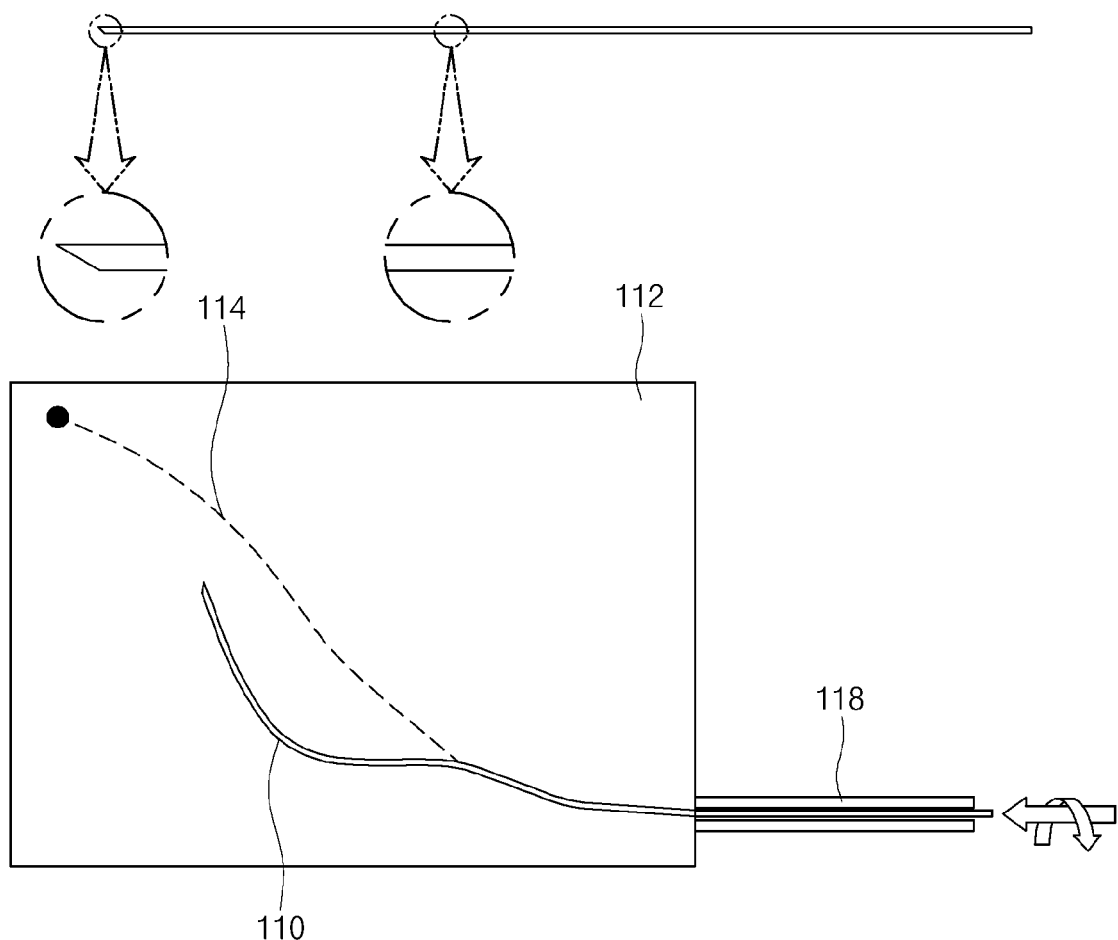
FIG. 1 shows the buckling phenomenon of a flexible needle.

The specific structural or functional descriptions presented in embodiments of the present invention are intended merely to describe the embodiments according to the concept of the present invention. The embodiments according to the concept of the present invention may be implemented in various forms. The present invention should not be construed as being limited to the embodiments described herein, and it should be understood that the present invention includes all changes, equivalents, or substitutes that do not depart from the spirit and technical scope of the present invention.

Meanwhile, although the terms "first," "second," etc. are used herein to describe various components, these components should not be limited by these terms. These terms are used merely to distinguish one component from another component. For example, a first component may be referred to as a second component, and the second component may be referred to as the first component, without departing from the spirit and scope of the invention as defined in the following claims.

It will be understood that when a component is described as being "connected" or "coupled" to another component, it can be directly connected or coupled to the other component or, instead, one or more intervening components may be present. In contrast, when a component is described as being "directly connected" or "directly coupled" to another component, there are no intervening components present. Other expressions used to describe the relationships between components, i.e., "between ~, and "immediately between ~," or "adjacent to" and "immediately adjacent to ~," should also be interpreted in a similar manner.

The same reference numerals designate the same components throughout the specification. Meanwhile, the terms used herein are intended merely to describe embodiments, and are not intended to limit the present invention. A singular form may include a plural form unless otherwise defined. The terms, including "comprise," "include," "comprising," "including" and their derivatives, specify the presence of one or more described components, steps, operations, and/or components, and do not exclude the presence or addition of one or more other components, steps, operations, and/or components.

The present invention will be described in detail below with reference to the accompanying drawings.

An adjustable-bending stiffness steerable needle according to the present invention includes a tip portion, a needle shaft, a compression spring, and a rigid shaft.

Figure 2:
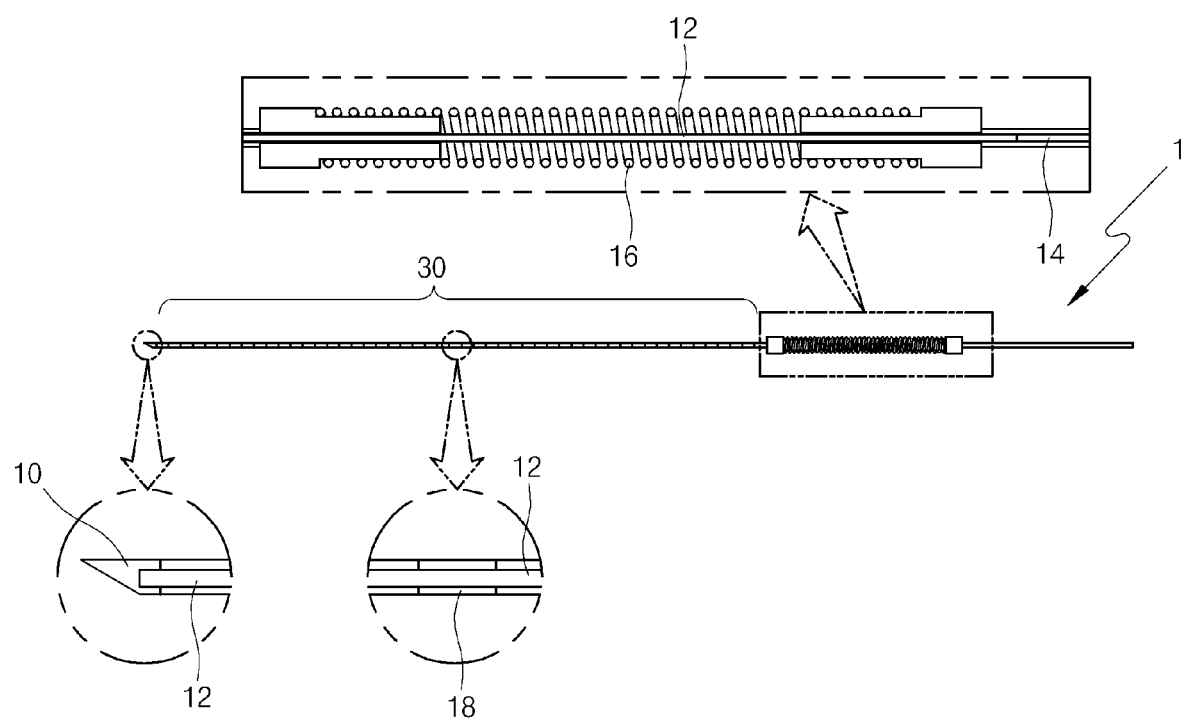
FIG. 2 shows an adjustable-bending stiffness steerable needle according to an embodiment of the present invention.

As shown in FIG. 2, an adjustable-bending stiffness steerable needle 1 according to an embodiment of the present invention may include: a cylindrical core wire 12; a bevel-shaped tip portion 10 connected to the front end of the core wire 12; a needle shaft 30 disposed such that one end thereof is separable from the tip portion 10 and the needle shaft 30 surrounds the core wire 12; a compression spring 16 fastened to the other end of the needle shaft 30, and configured such that the core wire 12 passes therethrough; and a rigid shaft 14 connected to the core wire 12 having passed through the compression spring 16, and also connected to the compression spring 16; wherein the needle shaft 30 may include a plurality of hollow tube elements 18 that are separable from each other.

As shown in FIG. 2, the bevel-shaped tip portion 10 is fixedly connected to one end of the core wire 12. The core wire 12 may be connected to the very end of the end portion of the tip portion 10, or may pass through at least part of the tip portion 10 and be fixedly connected to the tip portion 10. Furthermore, the tip portion 10 adjoins the coaxial tube elements 18 that surround the outer circumferential surface of the needle shaft 30 or core wire. Alternatively, the tip portion 10 separably comes into contact with the tube elements 18.

As shown in FIG. 2, the needle shaft 30 is connected to the tip portion 10. Preferably, the needle shaft 30 is separably connected to the tip portion 10. The needle shaft 30 may include a plurality of tubular tube elements 18. Each of the tube elements 18 is a tube considerably shorter than the needle shaft 30, and has a hollow hole therein. The plurality of tube elements 18 surrounds the core wire 12, and is disposed in the lengthwise direction of the needle shaft 30 in a line, thereby forming the needle shaft 30. Furthermore, each of the tube elements 18 is disposed to be separable from its adjoining tube element 18, and gaps or narrow spaces may be formed between the tube elements 18 by the bending of the core wire 12 or the like.

Referring to FIG. 2, the rear end of the core wire 12, i.e., the end of the core wire 12 opposite the end of the core wire 12 connected to the tip portion 10, is connected to the rigid shaft 14. Preferably, the core wire 12 is fixedly connected to the rigid shaft 14.

As shown in FIG. 2, the compression spring 16 is disposed between the needle shaft 30 and the rigid shaft 14. The front end of the compression spring 16 is connected to the needle shaft 30, and the rear end of the compression spring 16 is connected to the rigid shaft 14. The compression spring 16 is formed such that the core wire 12 passes through the compression spring 16.

Figure 3:
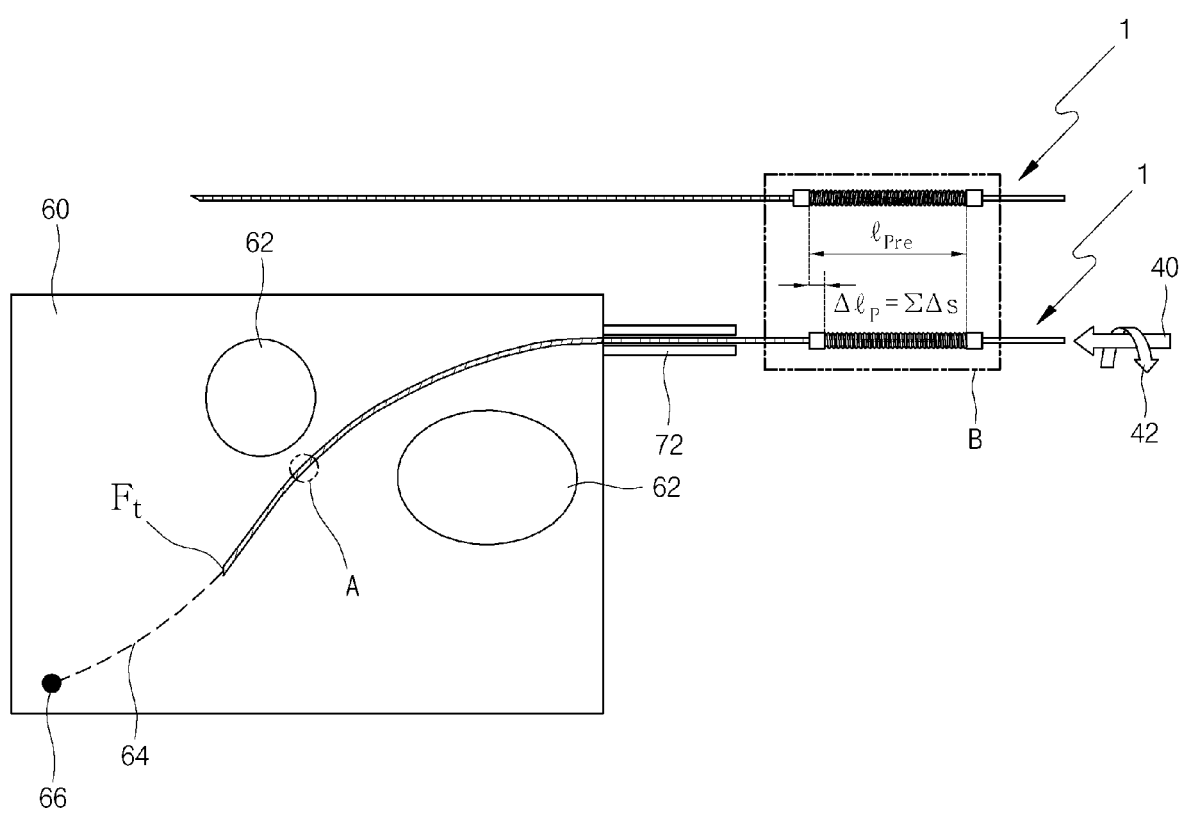
FIG. 3 shows a passively adjustable-bending stiffness steerable needle system according to an embodiment of the present invention.

Referring to FIG. 3, a steerable needle system according to an embodiment of the present invention may include: a steerable needle 1; an insertion driving unit 40 configured to insert the steerable needle 1 into a soft tissue 60; and a rotation driving unit 42 configured to rotate the steerable needle 1 inside the tissue. Furthermore, the steerable needle system according to the present embodiment may further include a compressing mechanism 44 configured to allow the compression spring 16 to be selectively extended and compressed with respect to the rigid shaft 14.

The insertion driving unit 40 may be preferably a mechanism configured to simultaneously insert the core wire 12, the needle shaft 30, and the compression spring 16, and the rotation driving unit 42 may be preferably a configuration configured to simultaneously rotate the core wire 12, and the compression spring 16. The compressing mechanism 44 may be a mechanism configured to generate relative movement between the core wire 12, connected to the tip portion 10, and the compression spring 16.

Figure 7:
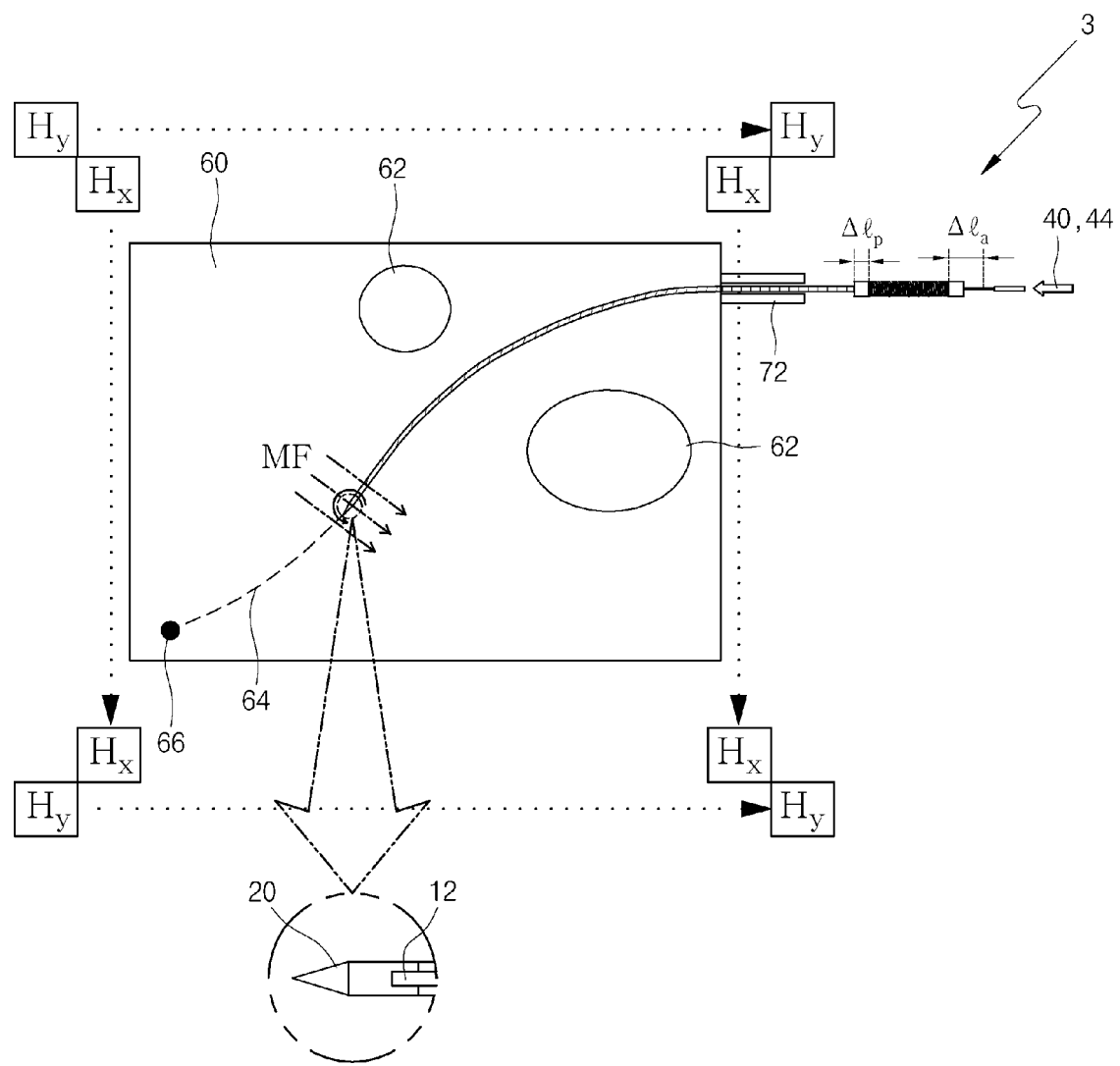
FIG. 7 shows an adjustable-bending stiffness steerable needle according to another embodiment of the present invention.

As shown in FIG. 7, an adjustable-bending stiffness steerable needle 3 according to another embodiment of the present invention may include: a cylindrical core wire 12; a tip portion 20 connected to the front end of the core wire 12; a needle shaft 30 disposed such that one end thereof is separable from the tip portion 20 and the needle shaft 30 surrounds the core wire 12; a compression spring 16 fastened to the other end of the needle shaft 30, and configured such that the core wire 12 passes therethrough; and a rigid shaft 14 connected to the core wire 12 having passed through the compression spring 16, and also connected to the compression spring 16; wherein the needle shaft 30 may include a plurality of hollow tube elements 18 that are separable from each other, and the tip portion 20 may be a cone-shaped permanent magnet that is steerable by an external magnetic field generation mechanism.

As shown in FIG. 7, the cone-shaped tip portion 20 composed of a permanent magnet is fixedly connected to one end of the core wire 12. The core wire 12 may be connected to the very end of the end portion of the tip portion 20, or may pass through at least part of the tip portion 20 and be fixedly connected to the tip portion 20. Furthermore, the tip portion 20 adjoins the coaxial tube element 18 that surrounds the outer circumferential surface of the needle shaft 30 or core wire. Alternatively, the tip portion 20 separably comes into contact with the tube element 18.

As shown in FIG. 7, the needle shaft 30 is connected to the tip portion 20. Preferably, the needle shaft 30 is separably connected to the tip portion 20. The needle shaft 30 may include a plurality of tubular tube elements 18. Each of the tube elements 18 is a tube considerably shorter than the needle shaft 30, and has a hollow hole therein. The plurality of tube elements 18 surrounds the core wire 12, and is disposed in the lengthwise direction of the needle shaft 30 in a line, thereby forming the needle shaft 30. Furthermore, each of the tube elements 18 is disposed to be separable from its adjoining tube element 18, and gaps or narrow spaces may be formed between the tube elements by the bending of the core wire 12 or the like.

Referring to FIG. 7, the rear end of the core wire 12, i.e., the end of the core wire 12 opposite the end of the core wire 12 connected to the tip portion 20, is connected to the rigid shaft 14. Preferably, the core wire 12 is fixedly connected to the rigid shaft 14.

As shown in FIG. 7, the compression spring 16 is disposed between the needle shaft 30 and the rigid shaft 14. The front end of the compression spring 16 is connected to the needle shaft 30, and the rear end of the compression spring 16 is connected to the rigid shaft 14. The compression spring 16 is formed such that the core wire 12 passes through the compression spring 16.

Referring to FIG. 7, a steerable needle system according to another embodiment of the present invention may include: a steerable needle 3; and an insertion driving unit 40 configured to insert the steerable needle 3 into a soft tissue 60. Furthermore, the steerable needle system according to the present embodiment may further include a compressing mechanism 44 configured to allow the compression spring 16 to be selectively extended and compressed with respect to the rigid shaft 14.

The insertion driving unit 40 may be preferably a mechanism capable of simultaneously inserting the core wire 12, the needle shaft 30, and the compression spring 16, and the compressing mechanism 44 may be a mechanism configured to generate relative movement between the core wire 12, connected to the tip portion 20, and the compression spring 16.

Since the detailed configurations of mechanisms for inserting and rotating a steerable needle by using a motor or the like are technologies well known in the technical field of needle steering, the present invention includes all configurations that can be adopted to insert and rotate a steerable needle by those skilled in the art, and detailed descriptions thereof are omitted herein.

According to the steerable needle 1 or 3 of the present invention, at least one of both ends of the compression spring 16 may be formed to be slidable along the outer circumferential surface of the core wire 12 so that the compression spring 16 can be compressed between the needle shaft 30 and the rigid shaft 14.

In other words, in order to passively control the bending stiffness of the steerable needle 1 or 3, only the front end or needle shaft 30-side end of the compression spring 16 may be formed to be slidable along the outer circumferential surface of the core wire 12. In contrast, in order to actively control the bending stiffness of the steerable needle 1 or 3, only the rear end or rigid shaft 14-side end of the compression spring 16 may be formed to be slidable along the outer circumferential surface of the core wire 12. Alternatively, in order to passively and actively control the bending stiffness of the steerable needle 1 or 3, the front and rear ends of the compression spring 16 may be formed to be slidable along the outer circumferential surface of the core wire 12.

Figure 4A:
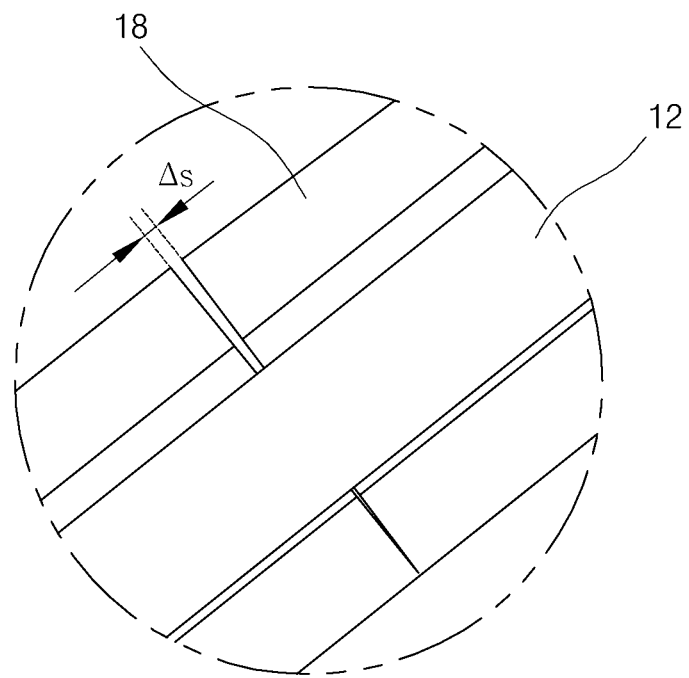
FIG. 4a is an enlarged view of portion A of FIG. 3.
Figure 4B:
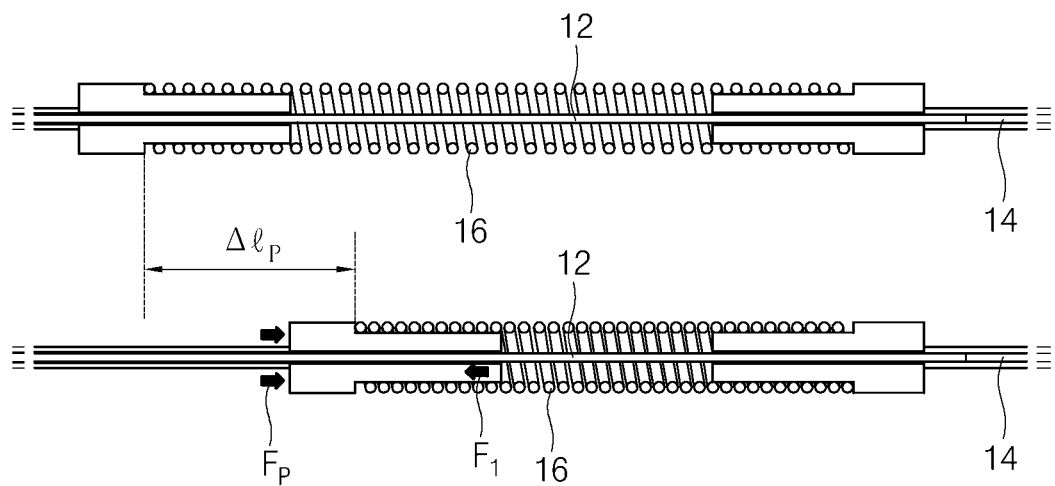
FIG. 4b is an enlarged view of portion B of FIG. 3.

Referring to FIG. 4b, in order to passively control the bending stiffness of the steerable needle, the needle shaft 30-side end of the compression spring 16 may be formed to be slidable along the outer circumferential surface of the core wire 12. When force $F_P$ is applied from a needle shaft 30 side, the needle shaft 30-side end or front end of the compression spring 16 slides along the outer circumferential surface of the core wire 12, and thus the compression spring 16 is compressed. Furthermore, the other end or rear end of the compression spring 16 connected to the rigid shaft 14 comes into tight contact with the rigid shaft 14.

Figure 5A:
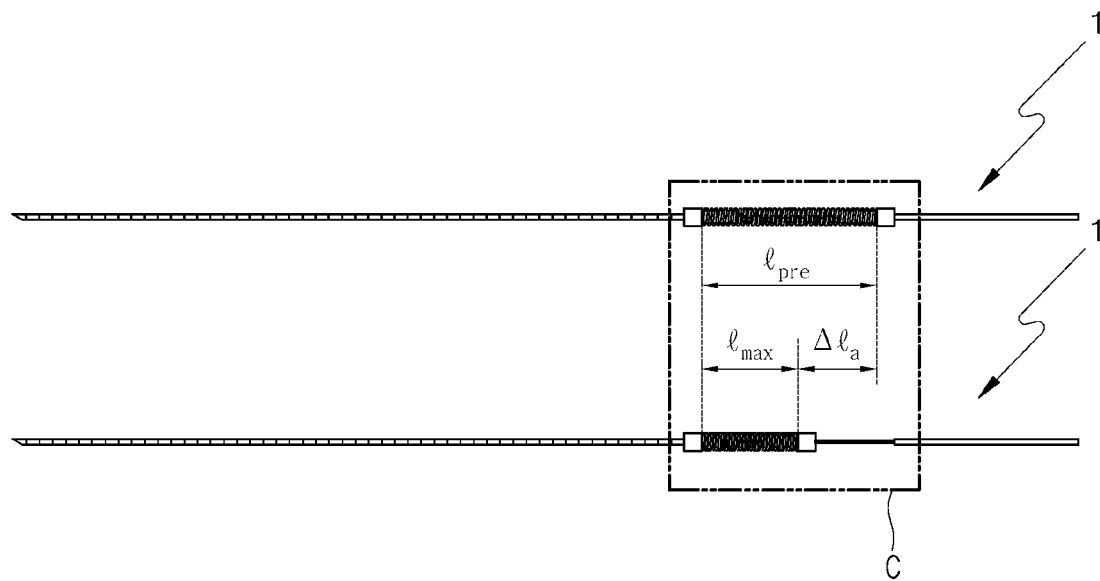
FIG. 5a shows the principle of the active bending stiffness control of a steerable needle system according to an embodiment of the present invention.
Figure 5B:
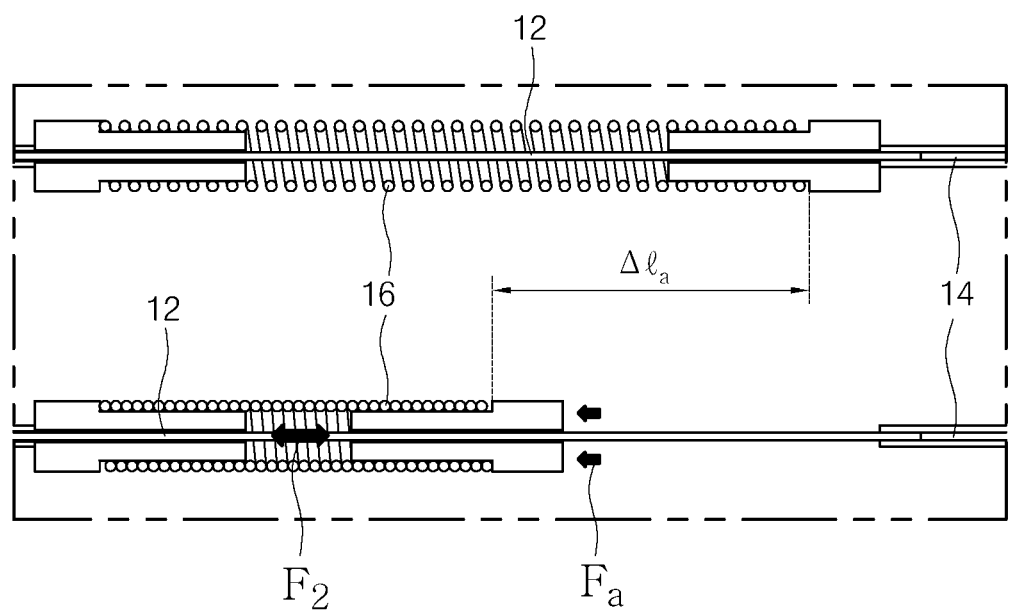

Furthermore, referring to FIG. 5b, in order to passively control the bending stiffness of the steerable needle, the rear end of the compression spring 16 is formed to be slidable along the outer circumferential surface of the core wire 12 when force $F_a$ is applied to the rear end of the compression spring 16 by the compressing mechanism 44 or the like. When force is applied in the direction of the compression spring 16 from a rigid shaft 14 side, the rigid shaft 14-side end of the compression spring 16 slides in the direction opposite the direction of the rigid shaft 14, and thus the compression spring 16 is compressed.

Furthermore, preferably, the bending stiffness of the steerable needle may be simultaneously controlled by using the above-described passive and active methods.

Referring to FIGS. 3, 4a, 4b and 7, a description is made of the principle by which the bending stiffness of steerable needle 1 or 3 according to the present invention is passively controlled such that, when the steerable needle 1 or 3 is inserted into the soft tissue 60, the steerable needle 1 or 3 can avoid an obstacle 62 and reach a target point 66 along a planned path 64. When the needle is inserted into the soft tissue 60, the bending of the needle is generated by interactive force $F_t$ between the bevel-shaped tip portion 10 or 20 and the soft tissue 60.

In this case, as shown in FIG. 4a, the sizes of the inner and outer curvatures of the needle shaft 30 become different, and thus small gaps Δs are generated between the tube elements 18. Furthermore, since the relative movement between the rigid shaft 14 fixedly connected to the core wire 12 and the compression spring 16 is restricted, the compression spring 16 is compressed from its original length $l_{Pre}$ by the sum $\Sigma \Delta s = l_P$ of the small gaps generated between the tube elements 18.

Accordingly, as shown in FIG. 4b, the distance $l_P$ by which the compression spring 16 is compressed changes in accordance with the magnitude of bending, and the bending stiffness of the steerable needle 1 or 3 is passively controlled by reaction force $\Sigma F_1 = k_s l_P$ (where $k_s$ is the elastic modulus of the compression spring) attributable to the compression of the compression spring 16 resulting from the pushing force $F_P$ of the needle shaft 30. Furthermore, in order to insert the needle in a steered manner, the steering angle of the needle may be adjusted by controlling the ratio between insertion and rotation in an axial direction.

Referring to FIGS. 5a, 5b, 6 and 7, a description is made of the principle by which the bending stiffness of steerable needle 1 or 3 according to the present invention is actively controlled such that, when the steerable needle 1 or 3 is inserted into the soft tissue 60, the steerable needle 1 or 3 can avoid an obstacle 62 and reach a target point 66 along a planned path 64. In order to actively control the bending stiffness, a structure to which the pressing mechanism 44 configured to generate relative movement between the core wire 12, connected to the tip portion 10 or 20 and the compression spring 16. In this case, the reaction force generated by the compression of the spring may be actively adjusted by actively controlling the distance $\Delta l_a$ by which the compression spring 16 is compressed.

Figure 6:
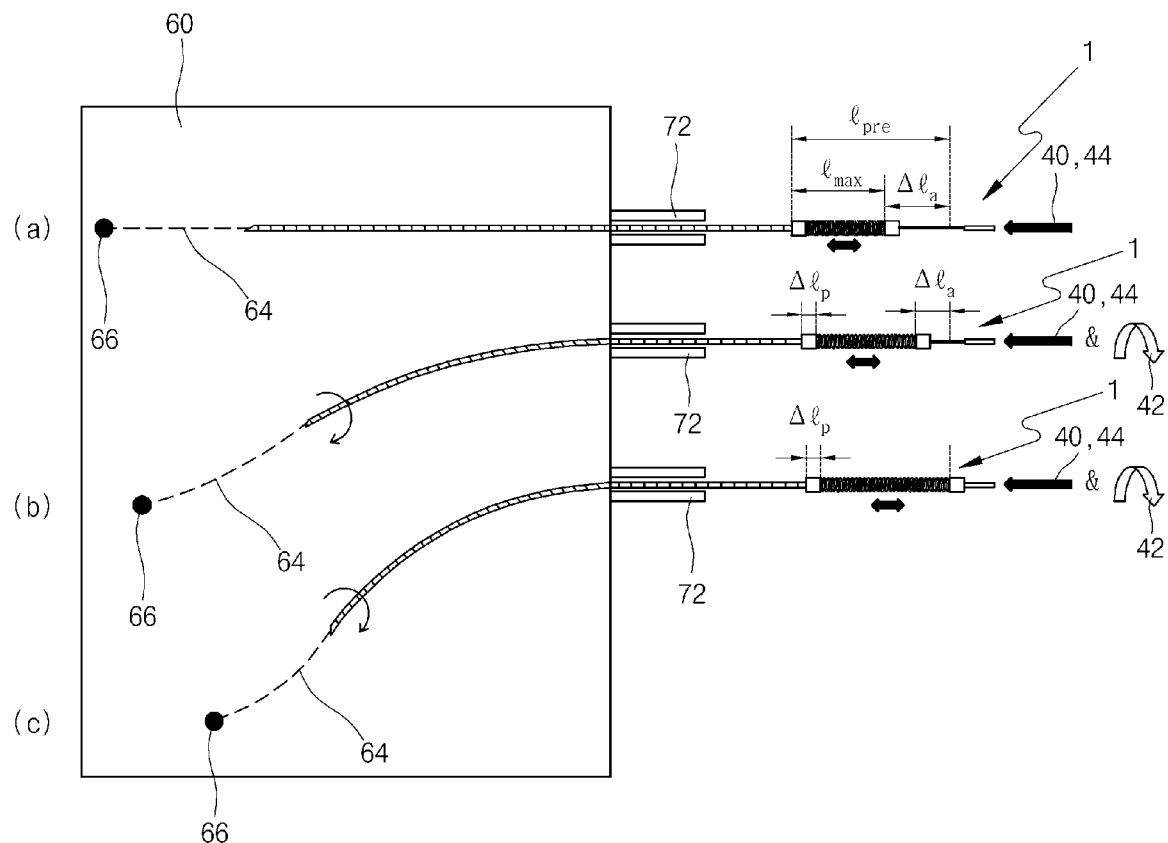
FIG. 6 shows the principle by which the bending stiffness of a steerable needle according to the present invention is adjusted.

In other words, as shown in FIG. 6, when the spring is maximally compressed (to $l_{max}$) through active control in order to steer the needle to the target point 66 along the planned path 64, the needle has bending stiffness similar to that of a conventional stiff needle (see upper view (a) of FIG. 6). Meanwhile, when the distance $\Delta l_a$ by which the spring is compressed becomes close to 0, the needle has a considerably flexible needle characteristic (see lower view (b) of FIG. 6).

Basically, the steering angle of the actively adjustable-bending stiffness steerable needle may be adjusted by controlling the ratio between the insertion of the needle and the axial rotation of the needle in the same manner as the steering angle of the above-described passively adjustable-bending stiffness steerable needle. Furthermore, the steering angle may be adjusted by minimizing axial rotation while actively adjusting the stiffness of the needle.

In other words, when the distance $\Delta l_a$ by which the spring is actively compressed is maximized, the needle is rectilinearly inserted in the same manner as the stiff needle (see upper view (a) of FIG. 6). Meanwhile, the needle may be steered and inserted along the planned path 64 by controlling the distance $\Delta l_a$ by which the spring is compressed (see views (b) and (c) of FIG. 6). Furthermore, the axial rotation of the needle may be minimized such that the direction of the tip portion 10 or 20 is changed only when an inflection point is present on the planned path 64.

According to the above-described method, the stress and damage caused by the axial rotation of the needle and applied to a soft tissue can be minimized. Furthermore, the needle can be more accurately moved to a desired location along a path having large curvature within a non-uniform soft tissue by substantially actively controlling the bending stiffness of the needle.

Referring to FIG. 7, the operation principle of a steerable needle 3 according to another embodiment of the present invention is now described. A tip portion 20 composed of a small cone-shaped permanent magnet instead of the bevel-shaped tip portion 10 is attached to a core wire 12. The attached permanent magnet may be actively steered in a desired direction by the driving of an external magnetic field generation mechanism, preferably an electromagnet or a permanent magnet, without requiring the axial rotation of the needle. In other words, the needle can be actively steered using a magnetic field MF formed by the external magnetic field generation mechanism without requiring a separate rotation mechanism. Furthermore, as described above, damage to a soft tissue may be minimized and more precise control may be performed by passively or actively controlling the bending stiffness of the steerable needle.

Figure 8:
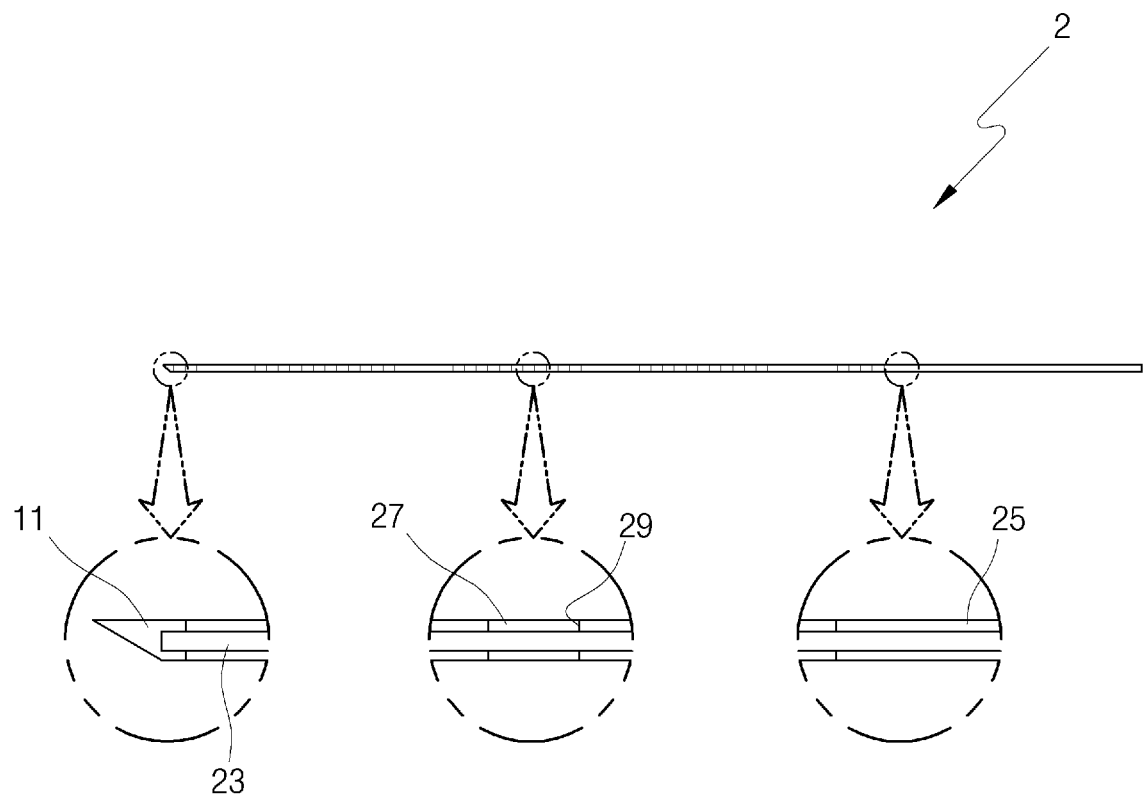
FIG. 8 shows a steerable needle according to another embodiment of the present invention.

Referring to FIG. 8, a buckling-preventing steerable needle 2 according to an embodiment of the present invention may include: a tip portion 11; a cylindrical core wire 23 configured such that one end thereof is connected to the tip portion 11; a rigid shaft 25 connected to the other end of the core wire 23; and a plurality of tube elements 27 disposed between the tip portion 11 and the rigid shaft 25 in a line in an axial direction while surrounding the core wire 23. One end portion of the tip portion 11 has a bevel shape, and the plurality of tube elements 27 is configured to be movable via gaps formed between the plurality of tube elements.

As shown in FIG. 8, the other end of the tip portion 11 one end portion of which has a bevel shape is fixedly connected to one end of the core wire 23. The core wire 23 may be connected to the very end of the other end portion of the tip portion 10, or may pass through at least part of the tip portion 11 and be fixedly connected to the tip portion 11. Furthermore, the other end portion of the tip portion 11 adjoins the coaxial tube elements 27 that surround the outer circumferential surface of the core wire 23.

As shown in FIG. 8, a rigid shaft 25 is fixedly connected to the other end of the core wire 23. Furthermore, the rigid shaft 25 adjoins the tube elements 27.

As shown in FIG. 8, the tube elements 27 are short tubes, and the term "plurality of tube element" indicates that tube elements 27 are plural in number. Gaps 29 are formed between the tube elements 27. The tube elements 27 are configured to be movable via the gaps 29 formed between the tube elements 27 so that the tube elements 27 can be passively and separately moved. Accordingly, the length of the core wire 23 may be equal to the sum of the overall length of the plurality of tube elements 27 and the overall length of all the gaps 29 formed between the tube elements 27.

Figure 10:
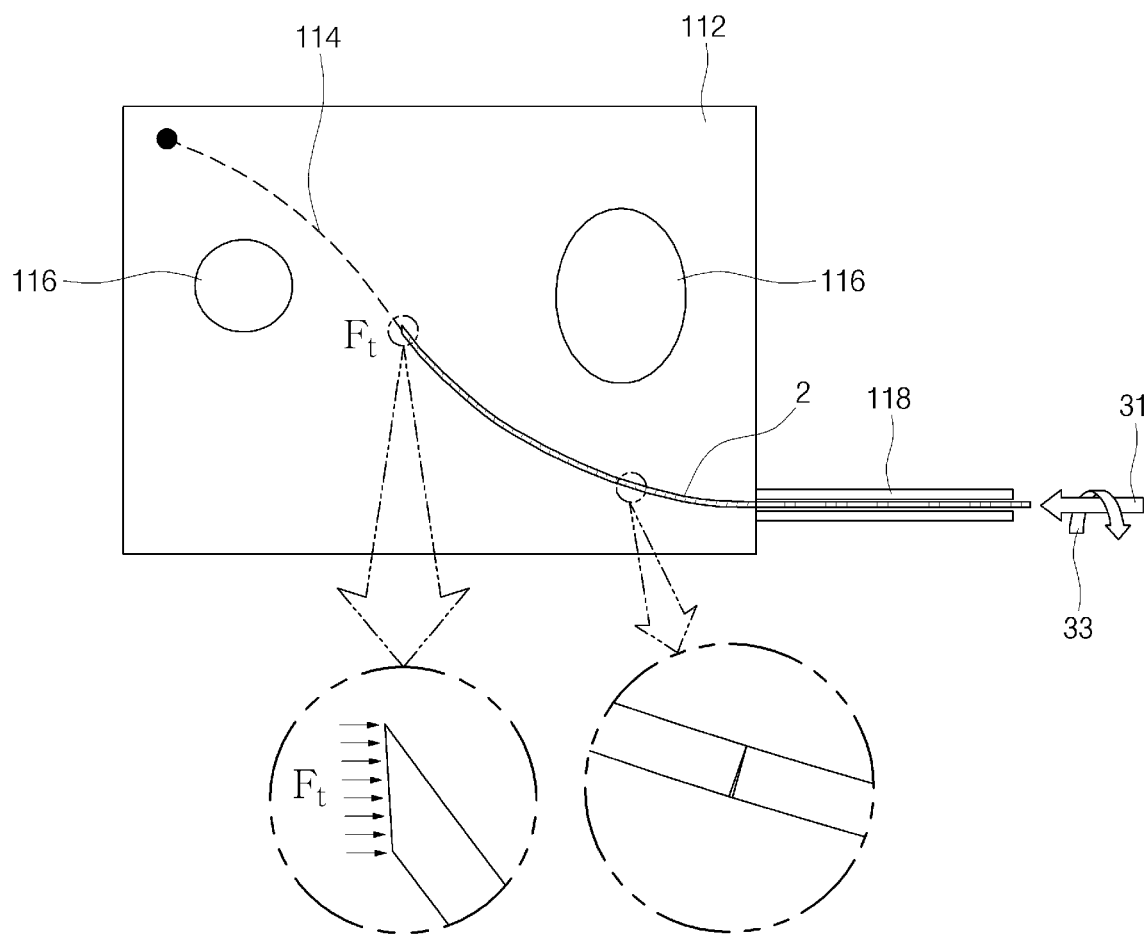
FIGS. 10 and 11 show the principle by which a steerable needle according to the present invention is prevented from being buckled.

As shown in FIG. 10, the buckling-preventing steerable needle 2 according to the present embodiment may further include at least one of an insertion mechanism 31 configured to insert the steerable needle 2 into a tissue and a rotation mechanism 33 configured to rotate the steerable needle 2 around an axial direction. The insertion mechanism 31 is preferably configured to simultaneously insert the core wire 23, the plurality of tube elements 27 and the rigid shaft 25. Furthermore, the rotation mechanism 33 is preferably configured to rotate the core wire 23 and the rigid shaft 25.

Figure 9:
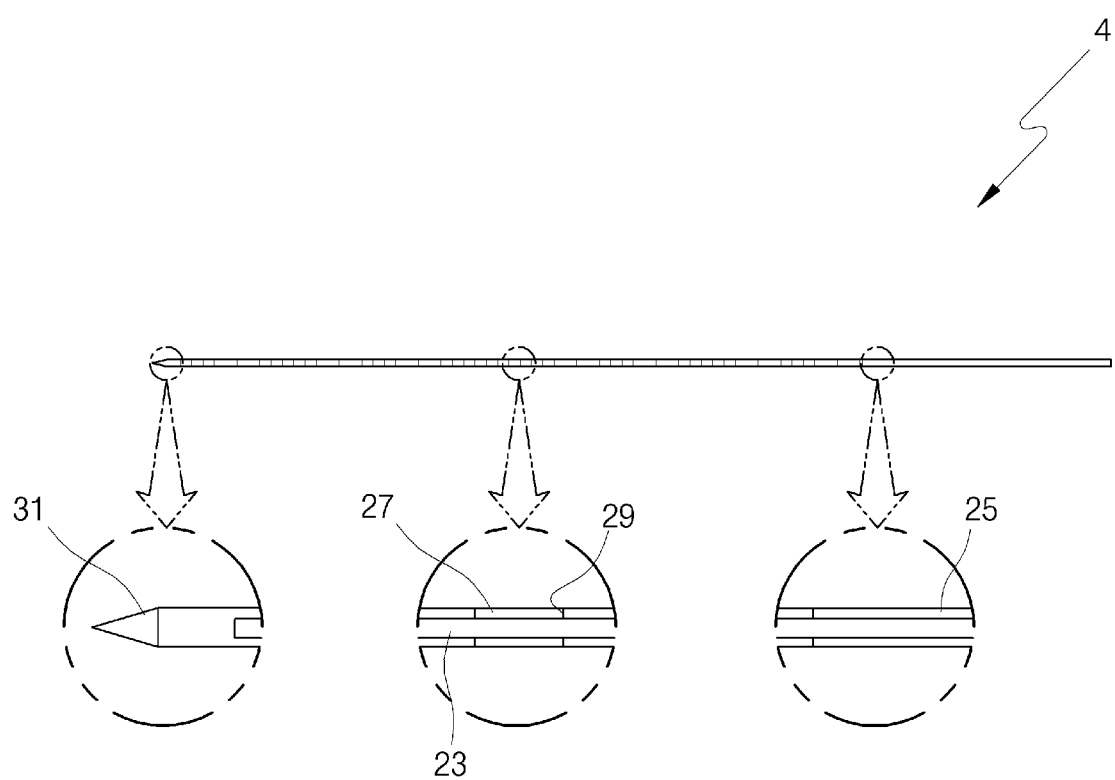
FIG. 9 shows a steerable needle according to another embodiment of the present invention.

Referring to FIG. 9, a buckling-preventing steerable needle 4 according to another embodiment of the present invention may include: a tip portion 31; a cylindrical core wire 23 configured such that one end thereof is connected to the tip portion 31; a rigid shaft 25 connected to the other end of the core wire 23; and a plurality of tube elements 27 disposed between the tip portion 31 and the rigid shaft 25 in a line in an axial direction while surrounding the core wire 23. The tip portion 31 has a cone-shaped one end portion, and is composed of a permanent magnet steerable by an external magnetic field generation mechanism. The plurality of tube elements 27 is configured to be movable via the gaps 29 formed between the tube elements 27.

As shown in FIG. 9, the other end portion of the tip portion 31 having the cone-shaped one end portion is fixedly connected to one end of the core wire 23. The core wire 23 may be connected to the very end of the other end portion of the tip portion 31, and may pass through at least part of the tip portion 31 and be fixedly connected to the tip portion 31. Furthermore, the other end portion of the tip portion 31 adjoins the coaxial tube elements 27 that surround the outer circumferential surface of the core wire 23. The tip portion 31 is an active steerable needle that is composed of a permanent magnet. The tip portion 31 is composed of a permanent magnet, and, thus, may be steered in a desired direction by an external magnetic field generation mechanism without requiring the axial rotation of the needle via a separate rotation mechanism. In this case, the magnetic field generation mechanism may be an electromagnet or a permanent magnet.

As shown in FIG. 9, the rigid shaft 25 is fixedly connected to the other end of the core wire 23. Furthermore, the rigid shaft 25 adjoins the tube elements 27.

As shown in FIG. 9, gaps 29 are formed between the tube elements 27. The tube elements 27 are configured to be movable via the gaps 29 formed between the tube elements 27 so that the tube elements 27 can be passively and separately moved. Accordingly, the length of the core wire 23 may be equal to the sum of the overall length of the plurality of tube elements 27 and the overall length of all the gaps 29 formed between the tube elements 27.

Referring to FIG. 10, the operation principle of the buckling-preventing steerable needle 2 according to the present embodiment is described below.

The steering angle of the steerable needle 2 according to the present invention may be adjusted by controlling the ratio between the insertion of the needle and the axial rotation of the needle in a manner similar to the manner in which the steering angle of a common flexible needle 110 having an oblique rear end is adjusted. In other words, steering is performed by controlling the insertion/translation speed of the needle in the lengthwise direction of the needle and the rotation speed of the needle around the lengthwise direction of the needle. In other words, the control of these variables may be performed by duty cycling. The duty cycling is performed to adjust the curved path of the moving needle by alternating a period in which the needle is inserted without rotation with a period in which the needle is inserted while being rotated. When the needle having a bevel-shaped tip is inserted without rotation, the needle follows a path having curvature depending on the characteristics (for example, stiffness, a bevel angle, etc.) of the needle and the characteristics (for example, density, uniformity, etc.) of a tissue. Furthermore, when the needle is moved at a sufficient rotation speed, the needle may be made to move along a rectilinear path. As described above, paths having various curvatures may be obtained by combining a period with rotation and a period without rotation.

When a set maximum curvature is reached upon insertion of the steerable needle 2, contact occurs in the one side gaps 29 between the tube elements 27, as shown in FIG. 10. Accordingly, for the needle 2 to be further bent (to be steered and inserted along a path having a larger curvature) after contact has occurred in the one side gaps 29 (a post-contact situation), considerably greater force is required, which serves to prevent the needle from being abruptly buckled.

Furthermore, referring to FIG. 10, before contact occurs in the one side gaps 29 of the steerable needle 2 (a pre-contact situation), the tube elements 27 may be passively and freely movable within the overall length of the core wire 23 due to the gaps 29 formed between the tube elements 27. In other words, bending in a pre-contact situation depends on the bending stiffness of the core wire 23, and thus the bending stiffness of the needle in this situation becomes considerably lower than that of a common steerable needle having the same outer diameter, with the result that improved steering performance is achieved using less force.

Accordingly, as shown in FIG. 10, it can be seen that the steerable needle 2 is steered along a planned path 114 without buckling while avoiding an obstacle 116 within a soft tissue 112.

Furthermore, during the axial rotation of the needle performed to control a steering angle, the tube elements 27 in direct contact with a soft tissue are not rotated, but only the needle tip portion 11 and the core wire 23 located within the plurality of tube elements 27 are rotated, and thus the stress applied onto the soft tissue due to the axial rotation can be minimized.

Figure 11:
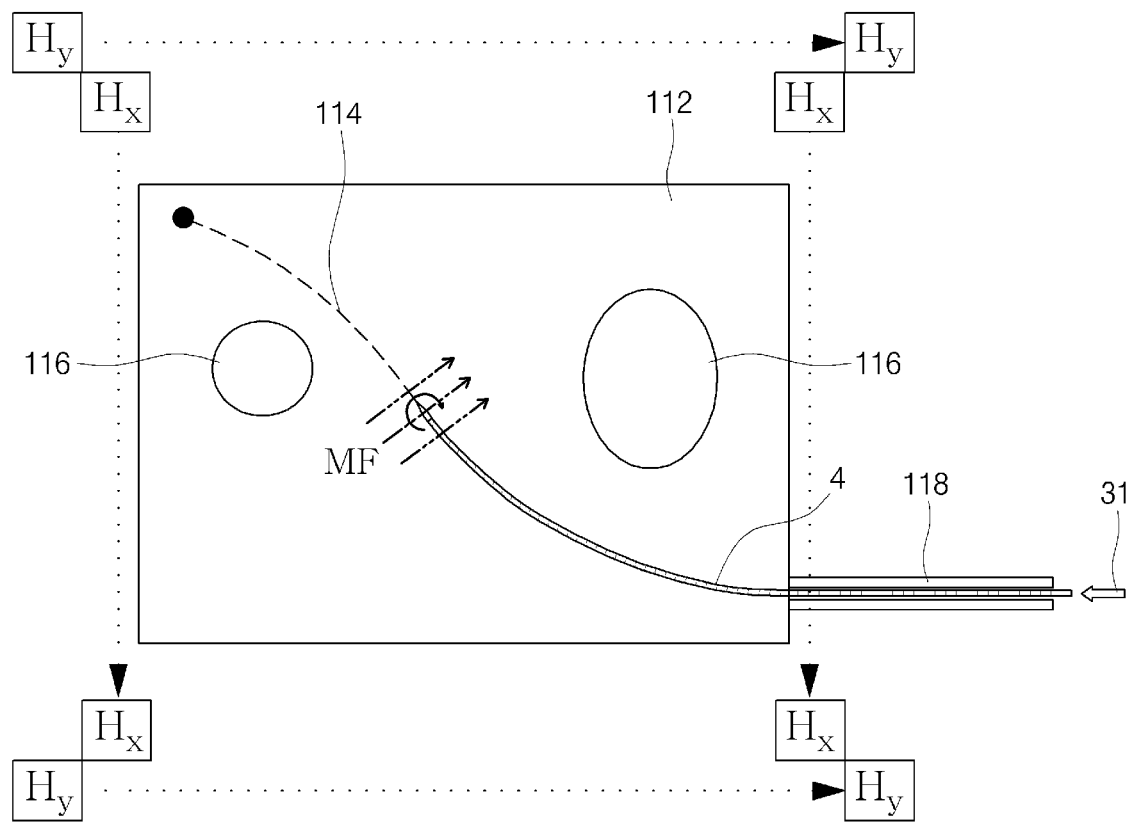

Furthermore, referring to FIG. 11, the steerable needle 4 having a cone-shaped tip portion according to the present invention is operated based on a principle similar to the principle by which the steerable needle 2 having a bevel-shaped tip portion is operated. The situation in which the steerable needle 4 is steered along the planned path 114 without buckling while avoiding the obstacle 116 within the soft tissue 112 is shown in FIG. 11. However, in this case, the steerable needle 4 having a cone-shaped tip portion is composed of a permanent magnet, and thus does not require a separate rotation mechanism. In other words, the needle is actively steered using a magnetic field MF, formed by an external magnetic field generation mechanism, without a rotation mechanism.

According to the adjustable-bending stiffness steerable needle of the present invention, an intervention treatment procedure can be more accurately and more effectively performed within a soft tissue through the active or passive control of the bending stiffness of the needle within the soft tissue.

According to the buckling-preventing steerable needle of the present invention, the improved steering performance of the needle can be provided within a soft tissue, and an intervention treatment procedure can be safely and stably performed within a soft tissue.

The present invention described above is not limited to the above-described embodiments and the accompanying drawings. It will be apparent to those having ordinary knowledge in the art to which the present invention pertains that various substitutions, modifications, and alterations can be made without departing the technical spirit of the present invention.

What is claimed is:

1. An adjustable-bending stiffness steerable needle, comprising:
    a cylindrical core wire;
    a tip portion connected to a front end of the cylindrical core wire;
    a needle shaft disposed such that a first end thereof is separable from the tip portion and the needle shaft surrounds the cylindrical core wire;
    a compression spring fastened to a second end of the needle shaft, and configured such that the cylindrical core wire passes therethrough; and
    a rigid shaft connected to the cylindrical core wire, and also connected to the compression spring,
    wherein the needle shaft includes a plurality of tube elements that are separable from each other, and the plurality of tube elements are arranged side by side between the tip portion and the compression spring along an axial direction of the cylindrical core wire, and a force generated by the compression spring is applied to the plurality of tube elements, and the plurality of tube elements come in contact with each other.

2. The adjustable-bending stiffness steerable needle of claim 1, wherein the tip portion has a cone-shaped permanent magnet, steerable by an external magnetic field generation mechanism.

3. An adjustable-bending stiffness steerable needle system, comprising:
    the steerable needle set forth in claim 2; and
    an insertion driving unit configured to insert the steerable needle into a tissue.

4. The adjustable-bending stiffness steerable needle of claim 2, wherein at least one of both ends of the compression spring is configured to be slidable along an outer circumferential surface of the cylindrical core wire.

5. The adjustable-bending stiffness steerable needle of claim 1, wherein at least one of both ends of the compression spring is configured to be slidable along an outer circumferential surface of the cylindrical core wire.

6. An adjustable-bending stiffness steerable needle system, comprising:
    the steerable needle set forth in claim 5;
    an insertion driving unit configured to insert the steerable needle into a tissue;
    a rotation driving unit configured to rotate the steerable needle within a tissue; and
    a compressing mechanism configured to allow the compression spring to be selectively extended and compressed with respect to the rigid shaft.

7. An adjustable-bending stiffness steerable needle system, comprising:
    the steerable needle set forth in claim 1;
    an insertion driving unit configured to insert the steerable needle into a tissue; and
    a rotation driving unit configured to rotate the steerable needle within a tissue.

8. The adjustable-bending stiffness steerable needle of claim 1, wherein the tip portion has a bevel shape.

* * * * *